US005549928A

United States Patent [19]

Trokhan et al.

[11] Patent Number: 5,549,928

[45] Date of Patent: Aug. 27, 1996

[54] PROCESS OF MAKING ABSORBENT STRUCTURES AND ABSORBENT STRUCTURES PRODUCED THEREBY

[75] Inventors: Paul D. Trokhan, Hamilton; Dean V. Phan, West Chester, both of Ohio

[73] Assignee: The Procter & Gamble Company, Cincinnati, Ohio

[21] Appl. No.: 441,363

[22] Filed: May 15, 1995

Related U.S. Application Data

[62] Division of Ser. No. 154,667, Nov. 17, 1993, abandoned.

[51] Int. Cl.[6] .......... B05D 1/28

[52] U.S. Cl. .......... 427/265; 427/264; 427/275; 427/278; 427/285; 427/288; 427/361; 427/365; 427/428

[58] Field of Search .......... 427/264, 265, 427/275, 278, 285, 288, 361, 365, 428; 604/358, 368, 372, 380

[56] References Cited

U.S. PATENT DOCUMENTS

| | | | |
|---|---|---|---|
| 3,721,242 | 3/1973 | Krusko | 128/287 |
| 3,849,173 | 11/1974 | Drelich et al. | 117/62.1 |
| 4,008,353 | 2/1977 | Gross et al. | 428/522 |
| 4,061,846 | 12/1977 | Gross et al. | 526/16 |
| 4,071,650 | 1/1978 | Gross | 428/260 |
| 4,082,878 | 4/1978 | Boe et al. | 428/195 |
| 4,145,464 | 3/1979 | McConnell et al. | 428/171 |
| 4,293,600 | 10/1981 | Fink et al. | 427/385.5 |
| 4,310,593 | 1/1982 | Gross | 428/290 |
| 4,354,487 | 10/1982 | Oczkowski et al. | 128/156 |
| 4,559,050 | 12/1985 | Iskra | 604/368 |
| 4,715,918 | 12/1987 | Lang | 156/273.1 |
| 4,748,076 | 5/1988 | Saotome | 428/224 |
| 4,835,020 | 5/1989 | Itoh et al. | 427/389.9 |
| 4,842,927 | 6/1989 | Itoh et al. | 428/254 |
| 4,865,886 | 9/1989 | Itoh et al. | 427/342 |
| 4,880,419 | 11/1989 | Ness | 604/368 |
| 4,888,238 | 12/1989 | Katz et al. | 428/378 |
| 4,892,754 | 1/1990 | Itoh et al. | 427/54.1 |
| 4,994,053 | 2/1991 | Lang | 604/367 |
| 5,013,309 | 5/1991 | Baigas, Jr. et al. | 604/368 |
| 5,071,681 | 12/1991 | Manning et al. | 427/392 |
| 5,079,034 | 1/1992 | Miyake et al. | 427/45.1 |
| 5,171,391 | 12/1992 | Chmielewski et al. | 156/229 |
| 5,175,046 | 12/1992 | Nguyen | 428/198 |
| 5,281,207 | 1/1994 | Chmielewski et al. | 604/378 |

FOREIGN PATENT DOCUMENTS

| | | |
|---|---|---|
| 0262405 | 8/1987 | European Pat. Off. . |
| 0257308 | 3/1988 | European Pat. Off. . |
| 0291316A2 | 11/1988 | European Pat. Off. . |
| 0290814 | 11/1988 | European Pat. Off. . |
| 0293762 | 12/1988 | European Pat. Off. . |
| 0304952 | 3/1989 | European Pat. Off. . |
| 2222780 | 11/1973 | Germany . |
| 63-291908 | 11/1988 | Japan . |
| 1452325 | 10/1976 | United Kingdom . |

OTHER PUBLICATIONS

Patent application Ser. No. 08/153,863, Filed Nov. 17, 1993 In The Name of Phan; now U.S. Pat. No. 5,487,736, issue Date Jan. 30, 1996.

*Primary Examiner*—Shrive Beck
*Assistant Examiner*—Erma Cameron
*Attorney, Agent, or Firm*—Larry L. Huston; E. Kelly Linman; Jacobus C. Rasser

[57] ABSTRACT

A process for making an absorbent structure having a capillary substrate and regions of osmotic absorbent on the capillary substrate. The osmotic absorbent is cured from a liquid precursor applied to the capillary substrate. The capillary substrate has regions of topographically different elevations, taken normal to the plane of the capillary substrate. The capillary substrate is passed through a gap between a transfer roll and an anvil roll in a printing apparatus. The transfer roll has at liquid precursor on its periphery. The liquid precursor is applied to only the topographically elevated regions of the capillary substrate which contact the periphery of the transfer roll. By changing the topography of the capillary substrate, the liquid precursor can be applied to the capillary substrate in different pattern, without changing the transfer roll. This arrangement allows for absorbent structures having various patterns of osmotic absorbent on a capillary substrate to be readily produced with great flexibility in the manufacturing process.

13 Claims, 2 Drawing Sheets

20 24 24 34 32 26 36 38 22

PROCESS OF MAKING ABSORBENT STRUCTURES AND ABSORBENT STRUCTURES PRODUCED THEREBY

This is a divisional of application Ser. No. 08/154,667 now abandoned, filed on Nov. 17, 1993.

FIELD OF THE INVENTION

This invention relates to a process for producing an absorbent structure having both osmotic and capillary absorbing capabilities. More particularly, the process relates to a way to make an absorbent structure having a patterned combination of capillary and immobilized osmotic absorbing capabilities.

BACKGROUND OF THE INVENTION

Absorbent structures comprising a capillary absorbent substrate and having an osmotic absorbent applied thereto are known in the art. As used herein, a "capillary" absorbent absorbs liquids, such as water, by capillary attraction of the liquids due to the thermodynamic force of attraction between a liquid and the solid surface of the capillary medium. In contrast, as used herein, an "osmotic" absorbent absorbs liquids deposited thereon by transfer of the liquids across the periphery of the osmotic absorbent, forming a gelatinous substance which imbibes the liquids. As used herein, an "absorbent structure" refers to materials which, in combination, absorb liquids by both osmotic and capillary absorptions.

The osmotic absorbent may be made from monomers selected from the group consisting of acrylic acid, starch grafted acrylate co-polymers, etc. Such osmotic absorbent materials are commonly used as absorbent gelling materials or superabsorbers in disposable absorbent articles such as diapers and sanitary napkins. The osmotic absorbent may be applied to the capillary substrate in the form of a liquid precursor, to be later cured into an osmotic absorbent.

The capillary absorbent may be provided in the form of a substrate, for the osmotic absorbent to be later applied thereupon. Typically the capillary substrate is a generally planar, almost two-dimensional material, such as paper, nonwoven fabric, woven fabric, or even formed film.

Generally, the osmotic absorbent material may be applied to the capillary substrate as a fluid precursor, such as a liquid monomer, then crosslinked to form an absorbent polymeric material. Usually, the liquid precursor is applied to the capillary substrate in a fluid form and comprises some form of acrylic acid and acrylate salts.

Typically, the liquid precursor is applied to the capillary substrate by spraying impregnation, etc. to provide a uniform coating thereon. Other teachings in the art suggest discontinuous applications of the liquid precursor to the capillary substrate through brushing, roller coating, etc. Once the liquid precursor is applied to the capillary substrate, the liquid precursor may be crosslinked through elevated temperature, irradiation, etc., to form the osmotic absorbent.

Examples of such attempts in the art include U.S. Pat. Nos.: 4,008,353 issued Feb. 15, 1977 to Gross et al.; 4,061,846 issued Dec. 6, 1977 to Gross et al.; 4,071,650 issued Jan. 31, 1978 to Gross; 4,835,020 issued May 30, 1989 to Itoh et al.; 4,842,927 issued Jun. 27, 1989 to Itoh et al.; 4,865,886 issued Sep. 12, 1989 to Itoh et al; 4,892,754 issued Jan. 9, 1990 to Itoh et al.; 5,079,034 issued Nov. 21, 1988 to Miyake et al. and Great Britain Patent 1,452,325 published October, 1976 in the name of Triopolis.

However, difficulties can arise in the prior art method of applying the liquid precursor to the capillary substrate. For example, it is difficult to spray the liquid precursor onto the capillary substrate in a precise pattern. Printing the osmotic absorbent onto the capillary substrate may result in a pattern having greater definition and precision than obtainable by spraying, but requires a printing roll having gravure plates or raised protuberances. Printing rolls having gravure plates or raised protuberances limit the pattern of the applied osmotic absorbent to that pattern corresponding to the gravure plates or the protuberances of the printing roll, regardless of what pattern may be desirable for a particular substrate.

This problem may be overcome by providing a plethora of printing rolls, one for each desired pattern. However, once the drying belt is fixed, such provision increases the expense of the apparatus to a point where it may not be economically feasible to provide a gravure roll or flexographic roll for each desired pattern if only a short production run is desired.

Accordingly, it is an object of this invention to overcome the problems presented by the prior art. Particularly, it is an object of this invention to provide an osmotic and capillary absorbent structure which resists gel blocking and which more efficiently utilizes the entire capacity of the absorbent structure. Further, it is an object of this invention to provide an absorbent structure which is more easily and precisely manufactured than those according to the prior art. Finally, it is an object of this invention to provide a process for manufacturing an absorbent structure having the osmotic absorbent registered with discrete regions of the capillary substrate.

SUMMARY OF THE INVENTION

The invention is a process for producing an absorbent structure having osmotic absorbing capability and capillary absorbing capability. The process comprises the steps of providing a transfer roll and an anvil roll. The two rolls are disposed, preferably in axially parallel relationship, so that a gap is formed between the two rolls. Liquid precursor is provided on the periphery of the transfer roll.

A capillary substrate is also provided. The capillary substrate is passed through the gap so that there is a relative difference in position within the gap between predetermined regions of the capillary substrate and corresponding regions of the transfer roll. The predetermined regions of the capillary substrate contact the corresponding regions of the transfer roll, so that liquid precursor is transferred from the corresponding regions of the transfer roll to the predetermined regions of the gap.

In a preferred embodiment, the capillary substrate has topographically elevated regions. The capillary substrate is passed through the gap between the transfer roll and the anvil roll, such that topographically elevated regions are oriented toward the transfer roll while the capillary substrate is in the gap. The capillary substrate rests against the anvil roll while it is passed through the gap between the transfer roll and the anvil roll. Liquid precursor is applied to the topographically elevated regions of the substrate from the periphery of the transfer roll while it is in the gap.

In an alternative embodiment, the transfer roll may have protuberances and the capillary substrate is generally planar and does not have topographically elevated regions. The liquid precursor is transferred from the protuberances of the transfer roll to the regions on the capillary substrate contacted by the protuberances.

The liquid precursor is then polymerized to form an immobilized osmotic absorbent on the substrate. The liquid precursor is polymerized in situ and thereby immobilized on the topographically elevated regions to which it was applied.

In a preferred embodiment, the process further comprises the steps of providing a metering roll and a reservoir. The liquid precursor is disposed in the reservoir. The metering roll is disposed, preferably in axially parallel and contacting relationship with the transfer roll, to form a nip between these two rolls. The metering roll is disposed in the liquid precursor in the reservoir, so that upon rotation of the metering roll liquid precursor is transferred from the reservoir to the periphery of the transfer roll for subsequent application to the capillary substrate.

BRIEF DESCRIPTION OF THE DRAWINGS

While the Specification concludes with the claims particularly pointing out and distinctly claiming the present invention, it is believed the present invention will be better understood from the following descriptions taken in conjunction with the accompanying drawings in which:

DETAILED DESCRIPTION OF THE INVENTION

Figure 1:
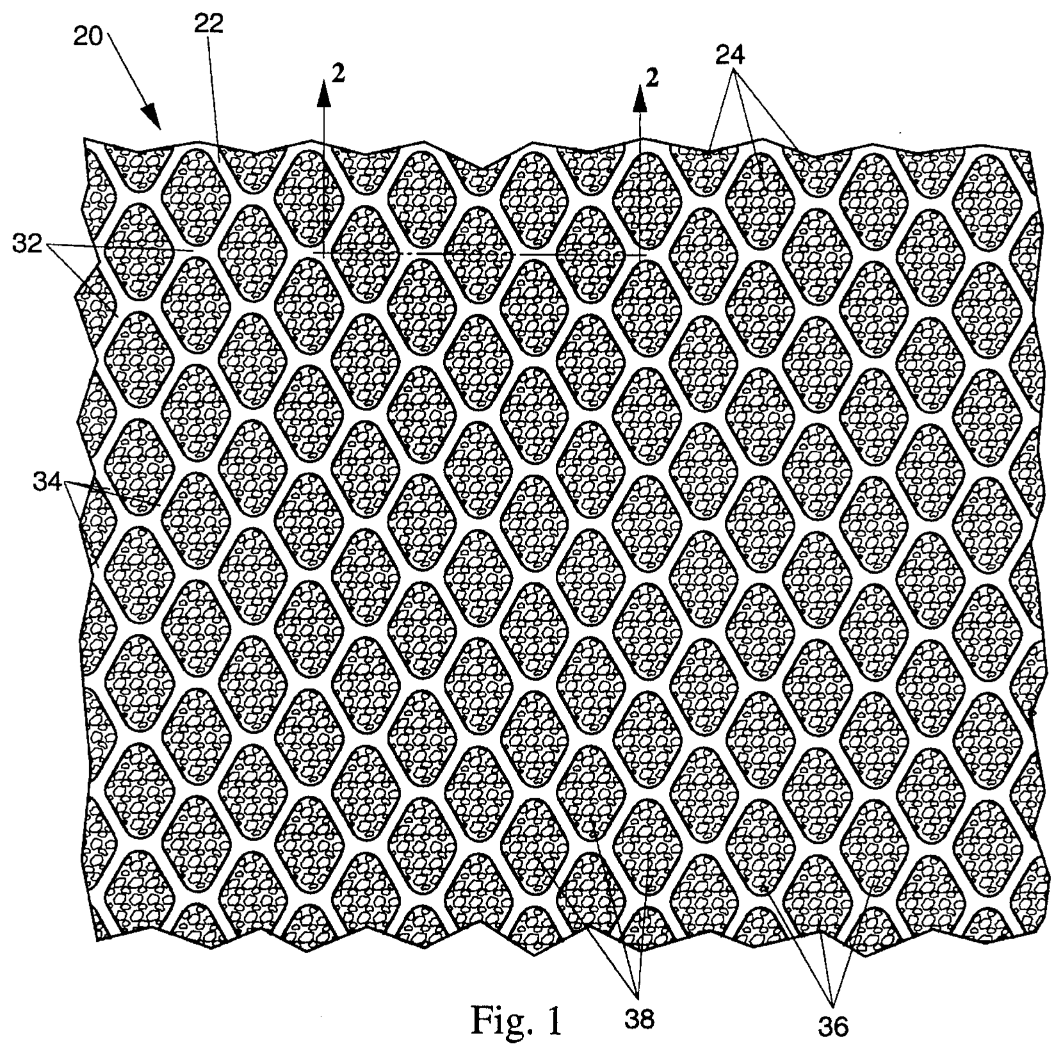
FIG. 1 is a fragmentary side elevational view of an absorbent structure according to the present invention having a capillary substrate with topographically elevated regions and discrete sites of osmotic absorbent material disposed on the topographically elevated regions.

An absorbent structure 20 made according to the process of the present invention comprises two subcomponents which are provided in a particular pattern as illustrated in FIG. 1: a capillary substrate 22 and an osmotic absorbent 24. The capillary substrate 22 has topographically distinguishable regions 34 and 38, differentiated by elevation 26 normal to the plane of the capillary substrate 22 and by being continuous or discrete. The osmotic absorbent 24 is applied to the topographically distinguishable regions 34 and 38 in a pattern corresponding to the elevation 26 of such regions 34 and 38.

The capillary substrate 22 may be provided with the topographically elevated regions 34 and 38 by through air drying a fibrous cellulosic capillary substrate 22 during the manufacturing process, by knob to knob embossing, by nested embossing or by laminating two laminae together. Through air drying is a particularly preferred process for producing a capillary substrate 22 having topographically elevated regions 36 and 38, because the regions 36 and 38 deflected from the plane of the capillary substrate 22 are discrete and have a lesser density than regions 32 and 34 which are not deflected.

The capillary substrate 22 preferably has a difference in elevation 26 between regions 34 and 38 sufficient to ensure the liquid precursor 40 is only applied to the desired regions 38. Preferably, the elevation 26 between the different regions 34 and 38 is at least about 0.13 millimeters (0.005 inches). The elevation 26 is measured without a confining pressure, using microtomoscopy or stereoscopic three-dimensional scanning electron microscopy imaging, as are well known in the art.

Figure 2:
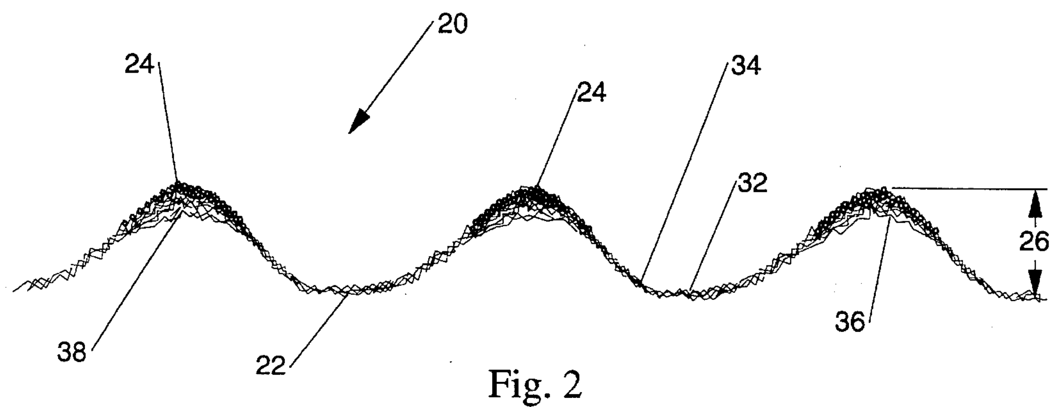
FIG. 2 is a fragmentary top plan view taken along line 2—2 of FIG. 1.

As illustrated in FIG. 2, the liquid precursor 40, which later cures to the osmotic absorbent 24, may be applied to the discrete topographically elevated regions 38 of the capillary substrate 22, leaving an essentially continuous network region 34 of the capillary substrate 22 without osmotic absorbent 24 thereon intermediate and circumscribing the discrete regions 36 to which the liquid precursor 40 is applied as set forth below. Of course, if the liquid precursor 40 is applied to the opposite face of the capillary substrate 22, the liquid precursor 40 will form an essentially continuous network region 34 and the capillary substrate 22 will have discrete regions 36 with no osmotic absorbent 24 thereon.

Embossing a single lamina yields a capillary substrate 22 having topographically elevated discrete regions 38 which are locally densified. If desired, the liquid precursor 40 may be applied to these regions, with less thermodynamic tendency to wick to the essentially continuous network region 32 than if the liquid precursor were applied to the regions of lesser density. However, as described above, through air drying is the preferred method of providing a capillary substrate 22 having topographically elevated regions 36 and 38.

Through air drying, knob to knob embossing, and nested embossing are illustrated in commonly assigned U.S. Pat. No. 4,529,480 issued Jul. 16, 1985 to Trokhan; commonly assigned U.S. Pat. No. 3,414,459 issued Dec. 3, 1968 to Wells; and U.S. Pat. No. 3,867,225 issued Feb. 18, 1975 to Nystrand, respectively. The foregoing three patents are incorporated herein by reference for the purpose of showing different ways to manufacture a capillary substrate 22 having topographically elevated regions 36 and 38.

The capillary substrate 22 made in accordance with the aforementioned U.S. Pat. No. 4,529,480 issued to Trokhan is particularly preferred because such a capillary substrate 22 has a continuous high density region 32 and discrete low density regions 36. Furthermore, the low density regions 36 are discrete regions 38 which have a difference in elevation 26 than the high density regions 32 which form a network region 34.

Figure 3:
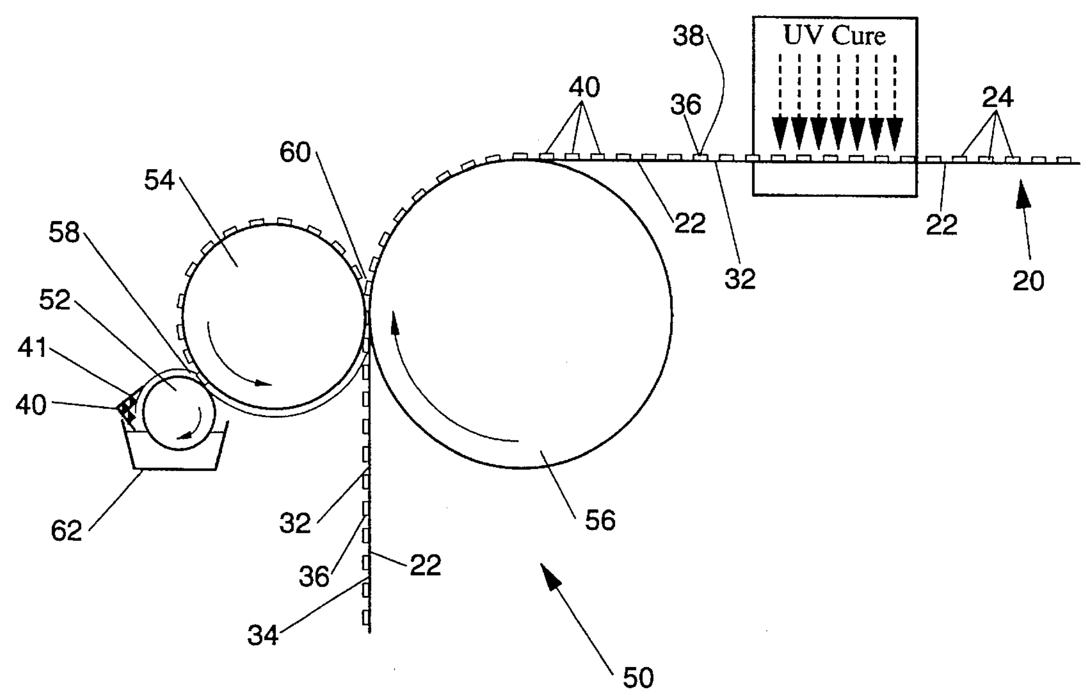
FIG. 3 is a schematic vertical elevational view of one apparatus which may be used to produce an absorbent structure according to the process of the present invention.

The osmotic absorbent 24 disposed on the capillary substrate 22 may comprise any osmotic precursor, typically a liquid precursor 40 which can be applied to the capillary substrate 22 as illustrated in FIG. 3. As used herein, a "precursor" refers to any material which transforms to an osmotic absorbent 24 upon curing or polymerizing. As used herein, an "osmotic absorbent" refers to any material which has the capability to absorb at least 10 times its own weight of aqueous liquids, preferably synthetic urine, on a grams per gram basis. Preferred osmotic absorbents 24 include polymers of sodium acrylate and acrylic acid, starch grafted acrylate copolymers, etc.

The synthetic urine comprises a salt solution in distilled water with a surface tension adjusted to 45 dynes per centimeter with about 0.0025% octylphenoxy polyethoxy ethanol surfactant (Triton X-100, from Rohm and Haas Company). The synthetic urine solution comprises 15 parts of 1% Triton X-100, 60 parts NaCl, 1.8 parts of $CaCl_2.2H_2O$, 3.6 parts of $MgCl_2.6H_2O$ and 6000 parts of distilled water.

Any liquid precursor 40 which can be cured into a solid osmotic absorbent 24 is suitable. The specific type of liquid precursor 40 selected is not critical to the invention, so long as the liquid precursor 40 may be applied in the desired pattern, and immobilized, so that the liquid precursor 40 does not flow, migrate, or transport to different elevations 26 of the capillary substrate 22. The osmotic absorbent 24 is preferably immobilized in both the dry condition and while wetted in use. A particularly preferred liquid precursor 40, and ultimately osmotic absorbent 24 for use in the present invention, comprises copolymers of sodium acrylate and acrylic acid, carboxymethyl cellulose, a photo-initiator and a cross-linker.

A preferred liquid precursor 40 is a substantially water-soluble monomer comprising neutralized or neutralizable carboxyl groups. The monomer preferably contains sufficient carboxyl groups such that a linear polymer thereof is substantially water-soluble (i.e., the carboxyl groups are hydrophilic). Mixtures of such monomers may also be used.

The monomers comprising carboxyl groups include acid, arthydride, and ester group containing monomers. These monomers may also contain other hydrophilic groups, such as hydroxyl groups, amide-groups, amino groups, nitrile groups, and quaternary ammonium salt groups. Preferably, the monomer contains acid type hydrophilic groups. More preferably, the monomer contains at least about 5 mole percent, most preferably at least about 10 mole percent, of acid groups.

Monomers containing carboxyl groups include the olefinically unsaturated acids, esters thereof, and anhydrides which contain at least one carbon to carbon olefinic double bond. More specifically, these monomers can be selected from olefinically unsaturated carboxylic acids, esters of such carboxylic acids, acid anhydrides, sulfonic acids, esters of such sulfonic acids, and mixtures of any two or more of the foregoing monomers.

Olefinically unsaturated carboxylic acid and carboxylic acid arthydride monomers include the acrylic acids and derivatives thereof, typified by acrylic acid itself, methacrylic acid, ethacrylic acid, alpha-chloroacrylic acid, alpha-cyano acrylic acid, beta-methyl acrylic acid (i.e., crotonic acid), alpha-phenyl acrylic acid, beta-acryloxy propionic acid, and beta-steryl acrylic acid; maleic acid; and maleic acid arthydride. Other monomers of this type are sorbic acid, alpha-chloro sorbic acid, angelic acid, cinnamic acid, p-chloro cinnamic acid, iraconic acid, citraconic acid, mesaconic acid, glutaconic acid, aconitic acid, fumaric acid, and tricarboxyethylene.

Olefinically unsaturated sulfonic acid monomers and derivatives thereof include aliphatic or aromatic vinyl sulfonic acids such as vinylsulfonic acid, allyl sulfonic acid, vinyltoluene sulfonic acid and styrene sulfonic acid, and acrylic and methacrylic sulfonic acid derivatives such as sulfoethyl acrylate, sulfoethyl methacrylate, sulfopropyl acrylate, sulfopropyl methacrylate, 2-hydroxy-3-acryloxy propyl sulfonic acid, 2-hydroxy-3-methacryloxy propyl sulfonic acid and 2-acrylamido-2-methyl propane sulfonic acid.

The carboxyl groups (e.g., acid groups) are at least partially neutralized with cations Is capable of forming a salt with the monomer to form a monomer having neutralized carboxyl groups, Such salt-forming cations include, for example, alkali or alkaline metals, ammonium, substituted ammonium and amines as discussed in further detail in U.S. Pat. Re. 32,649, Brandt et al., Apr. 19, 1988, incorporated herein by reference for the purpose of showing suitable osmotic absorbents 24. Neutralization is preferably carried out in any conventional manner which results in at least about 25 mole percent, more preferably at least about 50 mole percent, most preferably at least about 75 mole percent, of the total carboxyl groups being neutralized. The carboxyl groups are preferably neutralized prior to formation of the substantially water-insoluble polymer, e.g., neutralization is preferably carried out on the monomer or of a water-soluble polymer thereof.

Monomers possessing hydrophilic groups other than carboxyl groups may be used with the carboxyl group containing monomer, Other hydrophilic groups include hydroxyl groups, andde-groups, amino groups, nitrile groups, and quaternary ammonium salt groups. Monomers containing such groups are well known materials and are described in greater detail, for example, in U.S. Pat. No. 4,076,663 issued to Masuda et al. on Feb. 28, 1978; and U.S. Pat. No. 4,062,817 issued to Westerman on Dec. 13, 1977; which patents are incorporated herein by reference. One or more types of such hydrophilic groups may be present in the monomer.

Although this disclosure is generally in terms of the liquid precursor 40, it is to be understood that substantially water-soluble homopolymers, copolymers, or reaction products of the monomer may also be used in place of or in addition to the monomer form. Such alternative starting materials include substantially water-soluble homopolymers of the monomer and substantially water-soluble reaction products of the monomer or its homopolymer and the internal crosslinking agent. For example, a substantially linear, substantially water-soluble osmotic absorbent 24 can be formed by subjecting the liquid precursor 40 to known polymerization conditions. A substantially water-soluble, partially crosslinked osmotic absorbent 24 may also be formed by reacting (e.g., by heating) the liquid precursor 40 or linear polymer thereof with a crosslinking agent such as the crosslinking agents herein. Such an osmotic absorbent 24 would typically have a low level of crosslinking, e.g., less than about 5%.

To immobilize the liquid precursor 40 upon its application to the capillary substrate 22, or more particularly, upon application to selected regions of the capillary substrate 22, a thickening agent may be added to the liquid precursor 40 prior to application of the capillary substrate 22. Suitable thickening agents include polyvinyl pyrolodine, hydroxyethyl cellulose, preferably carboxymethyl cellulose and polyacrylic acid. The thickening agent may be added in a concentration of 2 percent by weight of thickening agent to the liquid precursor 40.

Preferably, the liquid precursor 40 has a kinematic viscosity of at least 2,000 centipoises, as measured by a Brookfield viscometer using a number 2 Shell cup at 20 degrees C. and preferably a kinematic viscosity of at least about 4,000 centipoises.

If one does not wish to add a thickening agent to the liquid precursor 40, an acrylic acid type liquid precursor 40 can be partially prepolymerized. Prepolymerization allows for removal of residual monomers before the liquid precursor 40 is applied to the capillary substrate 22. Minimizing residual monomers in the resulting osmotic absorbent 24 is highly desirable if the absorbent structure 20 is to be utilized in a disposable absorbent article, such as a diaper or sanitary napkin, or is to be utilized in other applications where epidermal contact may occur.

Immobilizing the liquid precursor 40 upon its application of the capillary substrate 22, or upon application to selected regions thereof, allows the liquid precursor 40 to be polymerized in situ. As used herein, a liquid precursor 40 is considered to be polymerized in situ if it is crosslinked or otherwise cured to form an osmotic absorbent 24 and thereafter occupies substantially the same location on the capillary substrate 22 as when originally applied thereto.

Referring to FIG. 3, the absorbent structure 20 according to the present invention may be made according to the illustrated apparatus 50. The illustrated apparatus 50 comprises three axially rotatable rolls 52, 54 and 56 preferably having mutually parallel longitudinal axes: a metering roll 52, a transfer roll 54, and an anvil roll 56. The three parallel rolls 52, 54 and 56 form a nip 58 and a gap 60. The nip 58 is between the metering roll 52 and the transfer roll 54. The gap 60 is between the transfer roll 54 and the anvil roll 56.

The metering roll 52 is a gravure roll disposed in a reservoir 62 of the liquid precursor 40. Upon axial rotation the metering roll 52 transfers a particular quantity of the liquid precursor 40 to the transfer roll 54. The capillary substrate 22 passes through the gap 60 between the transfer roll 54 having liquid precursor 40 disposed thereon and the anvil roll 56. Importantly the topographically elevated regions 36 and 38 of the capillary substrate 22, to which it is desired to apply the liquid precursor 40, are oriented towards the transfer roll 54, with the balance of the capillary substrate 22 resting against the anvil roll 56.

It will be apparent to one skilled in the art that by increasing or decreasing the clearance in the gap 60 between the transfer roll 54 and the anvil roll 56, smaller and larger quantities of the liquid precursor 40 may be applied to the topographically elevated regions 36 and 38 of the substrate, respectively. Likewise, changing the design of the metering roll 52 can alter the amount of liquid precursor 40 applied to the capillary substrate 22 at a constant gap 60. Alternatively, it will be apparent the liquid precursor 40 may be applied to the transfer roll 54 by spraying, submerging the transfer roll 54 in the liquid precursor 40, etc., and thereby eliminating the necessity for a metering roll 52, or by printing directly from the metering roll 52 to the substrate 22 in the gap 60 formed between the metering roll 52 and the anvil roll As the capillary substrate 22 passes through the gap 60 between the transfer roll 54 and the anvil roll 56, liquid precursor 40 is applied to only the regions 38 of the capillary substrate 22 which have an elevation 26 sufficient to contact the periphery of the transfer roll 54. The transfer roll 54, does not contact the regions 34 of the capillary substrate 22 which rest against the anvil roll 56. Accordingly, no liquid precursor 40 is applied to these portions of the capillary substrate 22.

As noted above, by adjusting the clearance in the gap 60, different quantities of the liquid precursor 40, and ultimately cured osmotic absorbent 24, may be applied to the elevated regions 36 and 38 of the substrate. Generally, for the embodiments described herein, liquid precursor 40 applied in the range of about 1 to about 500 milligrams per square centimeter of capillary substrate 22 have been found suitable. Generally, a greater quantity of osmotic absorbent 24 should be present on the capillary substrate 22 if the end use of the absorbent structure 20 dictates it will handle larger volumes of fluid. Generally a lesser quantity of the osmotic absorbent 24 should be present on the capillary substrate 22 if the end use of the absorbent structure 20 dictates concerns with gel blocking or the ability to rapidly transport fluid to other areas of the absorbent structure 20.

The capillary substrate 22 for a particular absorbent structure 20 is selected according to the trade-offs inherent in different factors (e.g., tensile strength, softness, absorbency) affecting the performance of the absorbent structure 20 for the consumer. The capillary substrate 22 is selected to optimize the performance factors, so that the consumer selects an absorbent structure 20 having the optimum performance.

Once the capillary substrate 22 to be utilized in the absorbent structure 20 is selected, based upon consumer preference, certain benefits become apparent. Particularly, the capillary substrate 22 according to the present invention, having regions of different elevations 26 (one elevational region 34 in contact with the anvil roll 56, the other elevational region 38 in contact with the transfer roll 54) provides several advantages not found in the prior art. First, a particular pattern of the liquid precursor 40 may be deposited onto the capillary substrate 22, without requiring the transfer roll 54 to have gravure plates or radially extending protuberances. Typically, transfer rolls 54 having patterns are more difficult to manufacture than smooth surfaced transfer rolls 54, and usually have a shorter life due to the wear of the protuberances.

A second benefit of the claimed invention is the flexibility one who may not wish to use a transfer roll 54 having a pattern, to achieve registration of the osmotic absorbent 24 with the regions of the capillary substrate 22 to which it was desired to dispose the liquid precursor 40. Either gravure plates or radially extending protuberances must be precisely registered with the regions 32 and 36 of a particular basis weight or density within the capillary substrate 22 to which it is desired to apply the liquid precursor 40. Such registration can be extremely difficult to achieve under even ideal manufacturing conditions, as the different regions 32 and 36 of the capillary substrate 22 often occur on near microscopic scale. Actual manufacturing is even more complex, because the pitch of the different regions 32 and 36, and hence the opportunity for misregistration may change with ordinary variations in tension as the capillary substrate 22 is drawn through the apparatus 50, the overall basis weight of the capillary substrate 22, and other manufacturing parameters. Production of the invention by the process depicted in FIG. 3, ensures exact registration of application of the liquid precursor 40 to the desired regions of the capillary substrate 22.

Third, one may wish to change the pattern of the liquid precursor 40 applied to the capillary substrate 22, and hence the pattern of the osmotic absorbent 24 on the resulting absorbent structure 20. According to the process of this invention, a single apparatus 50 having a transfer roll 54 with a smooth periphery may be utilized for multiple patterns. A capillary substrate 22 having a different topography is selected according to consumer preference and inserted in the gap 60 between the transfer roll 54 and anvil roll 56, and the clearance of the gap 60 adjusted as appropriate. The transfer roll 54 may continue to be provided with a smooth surface and any desired pattern achieved by simply changing the capillary substrate 22. Such flexibility in manufacturing was unattainable in the prior art.

After the liquid precursor 40 is disposed on the capillary substrate 22, or more particularly on topographically elevated regions 38 thereof, it is important the liquid precursor 40 be immobilized so that it does not flow into other regions 34 of the capillary substrate 22 and the desired pattern becomes diffused or imprecise. Immobilization occurs through curing the liquid precursor 40 using any suitable technique as is well known in the art. Particular and common techniques include electron beam irradiation and ultraviolet light. As noted above, it is desirable that the liquid precursor 40 be cured into an osmotic absorbent 24 as soon as possible after its application to the capillary substrate 22, minimizing the opportunity for liquid precursor 40 to flow into other areas of the capillary substrate 22. Minimizing the opportunity for the liquid precursor 40 to flow into the other areas of the capillary substrate 22 is particularly important if the topographically elevated regions 38 of the capillary substrate 22 to which the liquid precursor 40 is applied have a lower density than the topographically lower regions 34 of the capillary substrate 22 to which the liquid precursor 40 is not applied.

Curing, and in particular in situ curing, of the liquid precursor 40 can be accomplished by any means that initiates and causes polymerization of a free radical initiator such as 2-hydroxy-iso-butyrophenone or 2, 2-azobis (2-amidino propane) dihydrochloride is included in the monomer forming the liquid precursor 40, heat, light (either visible or ultraviolet radiation), or ionizing radiation can initiate and cause the polymerization reaction. If one desires, an osmotic chemistry which does not utilize a free radical initiator may be incorporated, thereby allowing any other appropriate initiator to be used. If one does not wish to include a free radical initiator, electron beam irradiation may be used to otherwise create free radicals which start the curing reaction. This curing process polymerizes and transforms the liquid precursor 40 into a solid osmotic absorbent 24 polymer. Thus, according to the present invention, the liquid precursor 40 is polymerized in situ without requiting an additional step between the application of the liquid precursor 40 and its polymerization to dispose and immobilize the osmotic absorbent 24 on the capillary substrate 22 in the desired location and pattern.

Several variations according to the present invention are feasible. For example, if desired, one may construct a capillary substrate 22 having an essentially continuous network region 34 and discrete regions 38 which differ according to basis weight rather than density. If such a capillary substrate 22 is selected, it may be advantageously made using a forming wire according to FIG. 4 of commonly assigned U.S. Pat. No. 4,514,345 issued Apr. 30, 1985 to Johnson et al., or the forming wires disclosed in U.S. Pat. No. 5,245,025 issued Sep. 14, 1993 to Trokhan et al., which patents are incorporated herein by reference for the purpose of showing how to make a capillary substrate 22 having regions 32 and 36 which differ according to basis weight. Alternatively, discrete regions 38 having plural different elevations 26 above (or below) the essentially continuous network regions 34 are feasible. The liquid precursor 40 may be applied to only the discrete regions 38 having a particular minimum elevation 26, or to each of the discrete regions 38 in elevation 26 dependent quantities.

Another variation involves the liquid precursor 40 which ultimately forms the osmotic absorbent 24. In this variation, it is recognized that osmotic absorbents 24 vary according to their gel strength i.e., the ability to retain absorbed fluids in the presence of compressive forces. Osmotic absorbents also vary according to absorption rate, i.e., the speed at which fluids deposited onto the osmotic absorbent 24 can be acquired and held thereby, and gel volume—the amount of fluid absorbed on a grams per gram basis. Generally, for a particular osmotic absorbent 24 the gel strength is inversely proportional to gel volume and absorption rate. If desired, an osmotic absorbent 24 having a more rapid absorption rate may be utilized at or near the center of the absorbent structure 20. Prophetically, in such an embodiment liquid insults are rapidly absorbed and do not readily flow to the perimeter of the absorbent structure 20 where leakage may occur if the liquids breach the perimeter.

Alternatively, the absorbent structure 20 may have an osmotic absorbent 24 with a faster absorption rate near the perimeter. This arrangement prophetically provides the advantage that liquids near the perimeter are rapidly absorbed before a breach of the perimeter can occur.

Similarly, the osmotic absorbent 24 near the center of the absorbent structure 20 may have a relatively greater gel strength. The relatively greater gel strength provides for relatively greater retention of liquid insults which are deposited near the center or the absorbent structure 20, so that such absorbed insults are less likely to approach the perimeter of the absorbent structure 20.

At or near the perimeter, an osmotic absorbent 24 having a higher gel strength but slower acquisition rate may be utilized. This osmotic absorbent 24 provides for greater retention of absorbed liquids, but can accommodate the slower acquisition due to the insult only being received indirectly by the perimeter since the liquid insult first occurs at the higher acquisition rate osmotic absorbent 24 disposed at or near the center of the absorbent structure 20. Either of the foregoing arrangements provides a transverse gradient with respect to the acquisition rate and gel strength properties of the osmotic absorbent 24 of the absorbent structure 20.

Prophetically, an absorbent structure 20 having osmotic absorbents 24 of differing gel strengths and/or acquisition rates may be made by utilizing a reservoir 62 having plural chambers. Each adjacent chamber contains a different liquid precursor 40. The chambers are made by inserting one or more machine direction oriented partitions in the reservoir 62. The partitions correspond to the desired boundaries or the different types of osmotic absorbent 24 in the resulting absorbent structure 20. Or course, the transfer roll 54 and anvil roll 56 are relieved in registration with the partitions, to obviate transfer of liquid precursor 40 between adjacent partitions.

A particularly preferred reservoir 62 has three chambers, spaced apart in the cross machine direction. The two outboard chambers each contain identical liquid precursor 40 having, by way of example, a relatively higher gel strength but relatively slower absorption rate upon polymerization. The central chamber contains a liquid precursor 40 having, by way or example, a relatively raster absorption rate but relatively low gel strength upon polymerization.

Or course, it will be apparent to one skilled in the art that the three (or any other number as desired) independent chambers need not be of equal width in the cross machine direction. The width or the chambers may be adjusted, as desired, to tailor the absorbent characteristics or the capillary substrate 22 or the resulting absorbent structure 20 to the needs dictated by the end use of the absorbent structure 20.

Prophetically, another process by which a transverse gradient of osmotic absorbent 24 properties may be imparted to the absorbent structure 20 utilizes multiple printing stations. At the first printing station, a transfer roll 54 and anvil roll 56 of a desired width and desired cross machine direction position are provided. The transfer roll 54 is immersed in a liquid precursor 40 having the particularly desired characteristics described above. This liquid precursor 40 is printed onto the capillary substrate 22 in register with the desired position (i.e., central trisection, etc.) and corresponding to the width and cross machine direction position of the transfer roll 54.

At the second printing station, another transfer roll 54 and anvil roll 56 are provided. This transfer roll 54 and anvil roll 56 are also registered at a particular cross machine direction position of the capillary substrate 22 and have a desired width. Of course, two outboard transfer rolls 54 and anvil rolls 56 may be used in tandem at a particular printing station of the apparatus 50.

In any event, multiple printing stations may be utilized, as described above, with one or more transfer rolls 54 and anvil rolls 56 at each printing station in order to produce an absorbent structure 20 having a transverse gradient with respect to the properties of the osmotic absorbent 24 according to the process of the present invention.

An arrangement of different osmotic absorbents 24 having a transverse gradient may be particularly useful if the absorbent structure 20 is incorporated into the core of a disposable absorbent article, such as a diaper, or a sanitary napkin. A disposable diaper utilizing the absorbent structure 20 of the present invention in the core may be made in accordance with commonly assigned U.S. Pat. No. 3,860, 003 issued Jan. 14, 1975 to Buell. Of course, the disposable diaper can be sized and configured to fit either children or incontinent adults, as desired, and as used herein is inclusive of disposable absorbent articles worn by either children or adults. A sanitary napkin utilizing the absorbent structure 20 of the present invention in the core may be made in accordance with commonly assigned U.S. Pat. No. 4,950, 264 issued Aug. 21, 1990 to Osborn, III. The aforementioned two U.S. Pat. Nos., 3,860,003 and 4,950,264, are incorporated herein by reference for the purpose of showing how to incorporate the absorbent structure 20 or the present invention into disposable absorbent articles. It will be apparent to one skilled in the art that several other variations are feasible, all of which are included within the scope of the appended claims.

What is claimed is:

1. A process for producing an absorbent structure having both osmotic and capillary absorbing capabilities, said process comprising the steps of:

providing a transfer roll and an anvil roll, said rolls being disposed in axially parallel relationship to form a gap therebetween;

providing a liquid precursor on the periphery of said transfer roll;

providing a capillary absorbent substrate, said capillary substrate having topographically elevated regions and being oriented so that said topographically elevated regions are oriented towards said transfer roll while said capillary substrate is in said gap, said capillary substrate resting against said anvil roll while in said gap;

passing said capillary substrate through said gap;

applying said liquid precursor from the periphery of said transfer roll to said topographically elevated regions of said substrate; and polymerizing said liquid precursor in situ to form an immobilized osmotic absorbent on said substrate.

2. The process according to claim 1 further comprising the steps of: providing a reservoir:

disposing said liquid precursor in said reservoir:

providing a metering roll in contacting relationship with said transfer roll, said metering roll and said transfer roll being juxtaposed to form a nip therebetween: and disposing said metering roll in said liquid precursor, whereby upon rotation of said metering roll liquid precursor is transferred from said reservoir to said metering roll to said periphery of transfer roll for application to said capillary substrate.

3. The process according to claim 1 wherein said elevated regions of said capillary substrate are discrete from one another.

4. The process according to claim 2, wherein said reservoir is divided into a plurality of independent chambers and further comprising a plurality of liquid precursors, each of said liquid precursors being disposed in one of said independent chambers, said liquid precursors having gel strengths and/or absorption rates, which, upon polymerizing are different from the gel strengths and/or absorption rates of the liquid precursors in other said independent chambers.

5. The process according to claim 4 wherein said reservoir is divided into plural independent chambers by trifurcating said reservoir into three chambers, two outboard chambers and a central chamber.

6. The process according to claim 5 wherein said liquid precursors deposited into said trifurcated reservoir comprises the step of providing a liquid precursor having a relatively higher gel strength in mid chamber reservoir than said liquid precursors in said outboard chambers and a liquid precursor having a relatively faster absorption rate in said outboard chambers than said liquid precursor in said central chamber.

7. The process according to claim 2 further comprising steps of:

providing a plurality of pairs of transfer rolls and anvil robs, skid pair having a transfer roll and an anvil roll disposed to form a gap therebetween;

providing a liquid precursor on the periphery of each said transfer roll;

passing said capillary substrate through said gaps between said pluralities of transfer rolls and anvil rolls; and applying said liquid precursor to said topographically elevated regions of said substrate, wherein the liquid precursor applied by one said transfer roll has different gel strengths and/or absorption rates than said liquid precursor applied by a different said transfer roll.

8. The process according to claim 7 wherein said plurality of transfer rolls comprises a first transfer roll which applies a centrally disposed liquid precursor to said capillary substrate; and two outboard transfer rolls which apply liquid precursor to said capillary substrate.

9. The process according to claim 1 further comprising the step of prepolymerizing said liquid precursor prior to its application to said substrate, thereby reducing residual monomers after polymerization.

10. The process according to claim 1 further comprising the step of adding a thickening agent to said liquid precursor.

11. The process according to claim 10 wherein said liquid precursor has a kinematic viscosity of at least about 4,000 centipoises at 20 degrees C. while in said reservoir.

12. The process according to claim 3 wherein said capillary substrate comprises a continuous high density region.

13. The process according to claim 12 wherein said capillary substrate further comprises discrete low density regions.

* * * * *

UNITED STATES PATENT AND TRADEMARK OFFICE

CERTIFICATE OF CORRECTION

PATENT NO. : 5,549,928

DATED : August 27, 1996

INVENTOR(S) : Paul D. Trokhan et al.

It is certified that error appears in the above-indentified patent and that said Letters Patent is hereby corrected as shown below:

| | |
|---|---|
| Column 5, lines 18, 36, 42 | delete "arthydride" and insert --anhydride--. |
| Column 5, line 44 | delete "iraconic" and insert --itaconic--. |
| Column 5, line 57 | --delete 1s-- |
| Column 6, line 9 | delete "andde" and insert --amide--. |
| Column 9, line 24 | delete "requiting" and insert --requiring--. |
| Col. 10, line 29 | "Or" should read --Of-- |
| Column 10 lines 7, 27, 39, 42, 45-47 | delete "or" and insert --of-- |
| Column 10, line 39 | delete "raster" and insert --faster--. |
| Column 11, line 24 | delete "or" and insert --of--. |
| Column 12, line 3 | after "said" insert --topographically--. |
| Column 12, line 21 | delete "mid" and insert --said central--. |

UNITED STATES PATENT AND TRADEMARK OFFICE

CERTIFICATE OF CORRECTION

PATENT NO. : 5,549,928

DATED : August 27, 1996

INVENTOR(S) : Paul D. Trokhan et al.

It is certified that error appears in the above-indentified patent and that said Letters Patent is hereby corrected as shown below:

Column 12, line 29 delete "robs, skid" and insert -- rolls, each said--.

Signed and Sealed this

Fifteenth Day of July, 1997

Attest:

BRUCE LEHMAN

*Attesting Officer* *Commissioner of Patents and Trademarks*